US005446030A

United States Patent [19]
Weisz et al.

[11] Patent Number: 5,446,030
[45] Date of Patent: * Aug. 29, 1995

[54] PREVENTION OF HEMOLYSIS

[76] Inventors: Paul B. Weisz, 3 Delaware Rim Dr., Yardley, Pa. 19067; Edward J. Macarak, 14 Winding Way, Glen Mills, Pa. 19342

[ * ] Notice: The portion of the term of this patent subsequent to May 28, 2008 has been disclaimed.

[21] Appl. No.: 762,606

[22] Filed: Sep. 19, 1991

[51] Int. Cl.$^6$ .................. A61K 31/56; A61K 31/715; C07H 1/00; C08B 37/16
[52] U.S. Cl. ..................... 514/58; 536/103; 514/832; 514/833
[58] Field of Search ............ 514/58, 832, 833; 536/103

[56] References Cited

U.S. PATENT DOCUMENTS

| | | | |
|---|---|---|---|
| 3,420,788 | 1/1969 | Solms | 260/17.4 |
| 4,020,160 | 4/1977 | Bernstein et al. | 424/180 |
| 4,066,829 | 1/1978 | Nair et al. | 536/103 |
| 4,247,535 | 1/1981 | Lewis et al. | 536/112 |
| 4,258,180 | 3/1981 | Lewis et al. | 536/112 |
| 4,352,794 | 10/1982 | Koch | 514/58 |
| 4,383,992 | 5/1983 | Lipari | 424/238 |
| 4,582,900 | 4/1986 | Brandt et al. | 536/103 |
| 4,596,795 | 6/1986 | Pitha | 514/58 |
| 4,703,042 | 10/1987 | Bodor | 514/58 |
| 4,727,064 | 2/1988 | Pitha | 514/58 |
| 4,764,604 | 8/1988 | Müller | 536/103 |
| 4,834,985 | 5/1989 | Elger et al. | 424/488 |
| 4,840,941 | 6/1989 | Ueno et al. | 514/59 |
| 4,877,774 | 10/1989 | Pitha et al. | 514/26 |
| 4,877,778 | 10/1989 | Carpenter et al. | 514/58 |
| 4,902,788 | 2/1990 | Zemel et al. | 536/1.1 |
| 4,983,586 | 1/1991 | Bodor | 514/58 |
| 5,002,935 | 3/1991 | Bodor | 514/58 |
| 5,017,566 | 5/1991 | Bodor | 514/58 |
| 5,019,562 | 5/1991 | Folkman et al. | 514/58 |
| 5,024,998 | 6/1991 | Bodor | 514/58 |
| 5,068,226 | 11/1991 | Weinshenker et al. | 514/58 |
| 5,100,878 | 3/1992 | Geber | 514/58 |
| 5,183,809 | 2/1993 | Weisz et al. | 514/58 |

FOREIGN PATENT DOCUMENTS

| | | |
|---|---|---|
| 0121777 | 10/1984 | European Pat. Off. . |
| 0188821 | 7/1986 | European Pat. Off. . |
| 0193850 | 9/1986 | European Pat. Off. . |
| 0325199 | 7/1989 | European Pat. Off. . |
| 0447171 | 9/1991 | European Pat. Off. . |
| 50-36422 | 4/1975 | Japan . |
| 50-140476 | 11/1975 | Japan . |
| 62-123196 | 6/1987 | Japan . |
| 63-122701 | 5/1988 | Japan . |
| 1315401 | 12/1989 | Japan . |
| WO85/02767 | 7/1985 | WIPO . |
| WO89/06536 | 7/1989 | WIPO . |

OTHER PUBLICATIONS

Alberts et al., "Molecular Biology of the Cell", Garland Publishing, Inc., New York, N.Y., 1983, pp. 702–709.
The Merck Index, Eleventh Edition, Susan Budavari et al. editor, Published by Merck & Co., Inc. Rahway, N.J., U.S.A., 1989, p. 256.
K. Uekama et al., *J. Pharm. Pharmacol.*, vol. 33, pp. 707–710 (1981).
W. Saenger, *Angew. Chem. Int. Ed. Engl.*, vol. 19, pp. 344–362 (1980).
K. Uekama et al., *Chem. Pharm. Bull.*, vol. 37, pp. 76–80 (1979).
Y. Sato et al., *Yakugazu Zasshi*, vol. 102 (1982) pp. 874–880.
T. Irie et al., *J. Pharm. Dyn.*, vol. 6, pp. 408–414 (1983).
K. Masuda et al., *Yakugazu Zasshi*, vol. 104, pp. 1075–1082 (1982).

(List continued on next page.)

*Primary Examiner*—Ronald W. Griffin
*Attorney, Agent, or Firm*—Duane, Morris & Heckscher

[57] ABSTRACT

Disclosed are compositions and methods for prevented or substantially inhibiting the hemolytic activity of hemolysis inducing agents. The methods and compositions are based on the use an anionic oligosaccharide, such as polysulfated cyclodextrin, to achieve the desired reduction in hemolytic active inducing agents.

10 Claims, 1 Drawing Sheet

OTHER PUBLICATIONS

T. Irie et al., *J. Pharm. Dyn.*, vol. 5, pp. 741–744 (1982).
J. Follezoa et al., *J. Biomed. Pharmacother.* vol. 36, pp. 326–328 (1982).
I. Jodal et al., *Proceedings of the Fourth International Symposium on Cyclodextrins*, O. Huber and J. Szejtli, Eds., 421–425, Kluwer Academic Publishers, Boston (1988).
*Clay and Clay Minerals*, vol. 34, pp. 74–80 (1986).
Nakashima et al., *Antimicrobial Agents and Chemotherapy*, pp. 1524–1528 (1987).
Uekama et al., *International Journal of Pharmaceutics*, vol. 10, pp. 1–15 (1982).
J. Pitha et al., *Journal of Pharmaceutical Sciences*, vol. 75(2), pp. 165–167 (1986).
Yamamoto et al., *International Journal of Pharmaceutics*, vol. 49, pp. 163–171 (1989).
*Chemical Abstracts*, 96:218351u (1982).
Croft et al., *Tetrahedron*, vol. 39, pp. 1417–1474 (1983).
Fenyvesi et al., *Chem. Pharm. Bull.*, vol. 32(2), pp. 665–669 (1984).
Fenyvesi et al., *Chem. Pharm. Bull.*, vol. 32(2), pp. 670–677 (1984).
Komiyama et al., *Polymer Journal*, vol. 18(4), pp. 375–377 (1986).
Herrmann, H. C., *Abstracts of Papers*, National Meeting of the American Heart Association, Anaheim, Calif.; Nov. 11–14, 1991.
*Chemical Abstracts* 83:79544a (1975).

PREVENTION OF HEMOLYSIS

FIELD OF INVENTION

This invention is concerned broadly with the prevention of damage to blood cells, particularly, erythrocytes. More specifically, the present invention is directed to the use of anionic oligosaccharides to prevent undesired hemolysis of blood cells, in the presence or absence of hemolytically active pharmacological agents. The present invention is also directed to novel non-hemolytic compositions, blood storage compositions and blood products comprising such anionic oligosaccharides.

BACKGROUND OF THE INVENTION

Hemolysis, damage to the structure of erythrocytes (red blood cells) resulting in a loss of hemoglobin, is generally undesired. Hemolysis can occur in vivo as the result of certain disease states or upon administration of certain therapeutic agents. In vitro, hemolysis can be induced during the handling and storage of blood, blood components or solutions, tissues or organs containing erythrocytes. Various chemical or pharmaceutical agents, as well as materials such as silica, clay, asbestos etc. can each cause hemolysis upon contact with erythrocytes. Because of their hemolytic properties, the use of many compounds and pharmaceutical agents that may have desirable pharmacologic properties may be limited in dosage or prevented from use altogether. For example, phenothiazine compounds are known to induce hemolysis above concentrations of the order of 0.1 mM. Chlorpromazine, a neuroleptic compound of the phenothiazine family exhibits hemolytic properties at concentrations in excess of 0.5 mM. Therefore the pharmaceutical use of chlorpromazine is restricted in dosage to avoid hemolytic side affects which would result at higher concentrations.

It has been previously reported that simultaneous use of 1.0 mM β-cyclodextrin inhibits the hemolytic action of chloropromazine. (K. Uekama et al., Protective Effects of Cyclodextrins on Drug-Induced Hemolysis In Vitro, Effects of Cyclodextrins on Chlorpromazine Induced Hemolysis and Central Nervous System Responses, J. Pharm. Pharmacol., 33:707–710 (1981)). It was shown that protection from hemolytic effects of the drug can be obtained by virtue of the ability of cyclodextrin to include the offending molecules within the cavity of the cyclic, doughnut shaped cyclodextrin molecule. This internal complexing capability of cyclodextrins has been widely recognized (see for example W. Saenger, Angew. Chem. Int. Ed. Engl., 19. 344–362 1980) and has been applied for the delivery of thereby solubilized pharmaceutical compounds (see for example, K. Uekama, F. Hirayama, K. Esaki, M. Inoue, Chem. Pharm. Bull., 37, 76–70, 1979). By virtue of such complexing, the outside solution concentration of the included agent is reduced, and, for sufficient cyclodextrin present, can be reduced below the critical concentration effective in hemolysis.

Similar uses of cyclodextrin to inhibit hemolysis have been reported for other pharmaceutical agents. Examples are described in the following articles: Improvement of Local Irritation Induced with Intramuscular Injection of Tiamulin by Cyclodextrin Complexation, Y. Sato et al., Yakugazu Zasshi, 102:874–880 (1982); Protective Mechanism of β-cyclodextrin for the Hemolysis Induced with Phenothiazine Neuroleptics In Vitro, T. Irie et al., J. Pharm. Dyn., 6:408–414 (1983); and Protective Effects of Cyclodextrin for the Local Irritation Induced by Aqueous Preparations of Flurbiprofen, K. Masuda et al., Yakugazu Zasshi, 104:1075–1082 (1982).

The use of β-cyclodextrin to inhibit hemolysis, however, is limited. It is now well recognized that β-cyclodextrin itself causes hemolysis at concentrations of about 2–3 mM and higher. Certain derivatives of β-cyclodextrin induce hemolysis at even lower concentrations. For example, when hydroxyl groups are replaced with O-methyl groups, hemolysis is observed at levels below 1 mM β-cyclodextrin. (T. Irie et al., Jr. Pharm. Dyn., 5:741–744 (1982)).

It is well known in the art (see the references to Saenger and Uekama noted above) that a molar quantity of cyclodextrin can include or host at most one but generally less than a molar quantity of pharmaceutical guest molecules. The quantity of pharmaceutical material that can be protected is therefore limited by the onset of hemolysis by the cyclodextrin concentration. Indeed, the beneficial effects of β-cyclodextrin reported to inhibit hemolytic activity of pharmaceutical agents in the aforementioned references uniformly were based on concentrations of β-cyclodextrin at or below 1.5 mM, and most frequently below 1.0 mM.

Aside from their use as hemolysis inhibitors, cyclodextrins, because of their unique inclusion capability and their water solubility, are useful for increasing the solubility of pharmaceutical agents of limited solubility by forming inclusion complexes with such agents. This application of cyclodextrin inclusion for solubilization of pharmaceutical or chemical agents of very low solubility is, of course, also limited in the amount of solubilization achievable, by the onset of hemolysis at the higher concentrations of cyclodextrins required, even though the agent itself is not hemolytically active.

OBJECTS OF THE INVENTION

Consequently it is an object of the present invention to provide methods of preventing hemolytic action on erythrocytes in a medium containing hemolytic irritants.

Another object of the invention is to provide non-hemolytic compositions for administration to mammals, including humans, containing hemolytic pharmaceutically active agents.

It is a further object of this invention to provide compositions containing chemical agents having demonstrated hemolytic activity and limited solubility, wherein the compositions possess reduced hemolytic activity and increased solubilization of the chemical agents.

Yet another object of the present invention is to provide compositions which are relatively non-hemolytic and which are useful for storing and preserving blood or blood-containing products.

These and other objects, aspects and advantages of the present invention will become apparent to those skilled in the art upon reviewing the following description and appended claims.

SUMMARY OF THE INVENTION

We have now found that cyclodextrins with polyanionic substitutions of their hydroxyl groups do not exhibit hemolytic activity, even at high aqueous concentrations. More surprisingly we have discovered that these substances will protect erythrocytes from the hemolytic effects of an unusually large spectrum of hemolytically active substances, including a large variety of hemolytically active pharmaceuticals, other irritants such as silicates, and the cyclodextrins themselves.

This invention provides methods of protecting erythrocytes from the hemolytic effects of a variety of agents which typically induce hemolysis, such as can occur upon storage and/or handling of blood or blood-containing products. Preferred methods comprise the step of contacting the erythrocytes, whether contained in whole blood, a blood solution, blood-containing product, tissue or organ, with a protective agent comprising an anionic oligosaccharide. According to highly preferred embodiments, the contacting step comprises contacting the erythrocytes with an isotonic solution containing a protective agent comprising a polyanionic oligosaccharide.

This invention further provides non-hemolytic compositions for administration to a patient in need of treatment with a potentially hemolytic pharmaceutical agent, the composition comprising: (1) an anionic oligosaccharide and (2) said pharmaceutical agent. Compositions for protecting erythrocytes from the effect of hemolysis inducing agents typically associated with the storage and handling of blood and/or blood containing products are also provided. Such compositions preferably comprise a polyanionic oligosaccharide and one or more additives useful for blood preservation. According to certain embodiments, such compositions preferably comprise β-cyclodextrin tetradecasulfate as the polyanionic cyclodextrin.

DETAILED DESCRIPTION OF THE INVENTION

Figure 1:
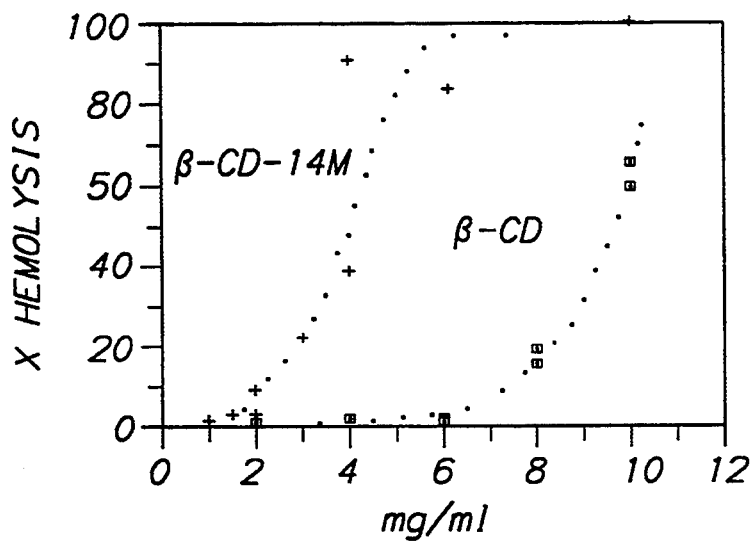

This invention is based, at least in part, on the finding that certain relatively simple and synthetically well reproducible oligosaccharides possesses two important characteristics: (1) an ability to prevent or substantially inhibit the hemolytic effect caused by a variety of hemolysis inducing agents and (2) a substantial absence of inherent hemolytic activity. In particular, Applicants have found that anionic oligosaccharides, and preferably polyanionic oligosaccharides, generally possess these beneficial characteristics. As used herein, the term anionic oligosaccharide refers to oligosaccharides having at least one anionic substituent and the term polyanionic oligosaccharide refers to oligosaccharides having two or more anionic substituents per molecule. The oligosaccharides are preferably saccharides of from about 5 to about 10 sugar units and have molecular weights, when unsubstiuted, from about 650 to about 1300. While Applicants contemplate that the anionic substituents of the present invention may be selected from a large group of known and available anionic substituents, it is generally preferred that the anionic substituents be selected from the group consisting of sulfate, carboxylate, phosphate and combinations of two or more of these. The anionic substituents are also preferably present in the molecule to an extent of from about 1.5 to about 3 substituents per sugar unit. Especially preferred compositions are those based on oligosaccharides having about 2 sulfate substituents per sugar unit. Other preferred compositions are based on oligosaccharides having from about 2 to about 3 substituents per sugar unit, wherein the substituents comprise sulfate and/or phosphate substituents.

Particularly preferred are those oligosaccharides commonly referred to as cyclodextrins. They are characterized by a cyclic structure of generally from about 6 to about 8 glucose units forming a ring or toroid shaped molecule which therefore has no end groups.

Oligosaccharides are chains of several sugar units such as glucose units, connected through glycosidic oxygen atoms. As used herein, the prefix "oligo" indicates an intermediate number of sugar or saccharide units, as compared to a monomeric sugar unit of one, or at most two as in sucrose, on one hand and a polysaccharide having twenty or more of sugar units and high molecular weight on the other hand. While all such oligosaccharides are believed to be operable within the scope of the present invention, the oligosaccharides hereof preferably have about five 5 to about 10 saccharide units per molecule. This range corresponds to unsubstituted saccharides having molecular weights ranging from about 650 to about 1300. Oligosaccharides having from about 5 to about 10 saccharide units per molecule are sometimes referred to herein as "simple" or "low molecular weight" oligosaccharides. Oligosaccharides are usually obtained by procedures of degradation of starches or cellulose which result in oligosaccharide fragments in a broad range of sizes.

A somewhat related family of materials of biological significance are the glycosaminoglycans. They are structures comprising a polysaccharide skeleton, modified by a great variety of substituents containing atoms of nitrogen, sulfur and oxygen, and comprising various segments such as glucosamines, iduronates, glucuronates, etc. Their structures are variable between different samples of the same name group, such as the chondroitans, dermatans, hyaluronic acid, heparan sulfates, and heparins. Each family is known to be heterogenous, i.e. mixtures of compositions. Their molecular weight ranges generally between 10,000 and 25,000. Many biological functions are ascribed to various of such materials, often also referred to as mucopolysaccharides. One case of inhibition of hemolysis is reported to have been observed for a heparin: Heparin inhibition of adriamycin-induced in vitro hemolysis. Follezoa, J. Y., Bizon, M. Gicquel, J. Biomed. Pharmacother., 36, 326–328, 1982.

We have now discovered that anionically substituted oligosaccharides, and especially the simple and low molecular weight oligosaccharides with anionic substituents, have remarkable effectiveness for protecting erythrocytes from hemolytic action. Our finding of the protective activity of anionically substituted oligosaccharides, such as sulfated cyclodextrin, was particularly surprising inasmuch as cyclodextrins themselves and many of their derivatives examined have been shown to themselves to be hemolytically active.

For illustration of the discovery and as background to the present invention, FIG. 1 graphically illustrates the hemolytic effects of the non-substituted oligosaccharide β-cyclodextrin (β-CD) and of the non-anionically substituted oligosaccharide β-CD with 14 methyl group substituents (β-CD-14M) on fresh human blood to which about 0.47% sodium citrate was added. The onset of hemolysis is near about 6 mg/ml for β-CD and near about 2 mg/ml for β-CD-14M. (Data for β-CD approaching 13 mg/ml is unreliable because the solubility limited limit is less than about 13 18 mg/ml at 20° C.)

Figure 2:
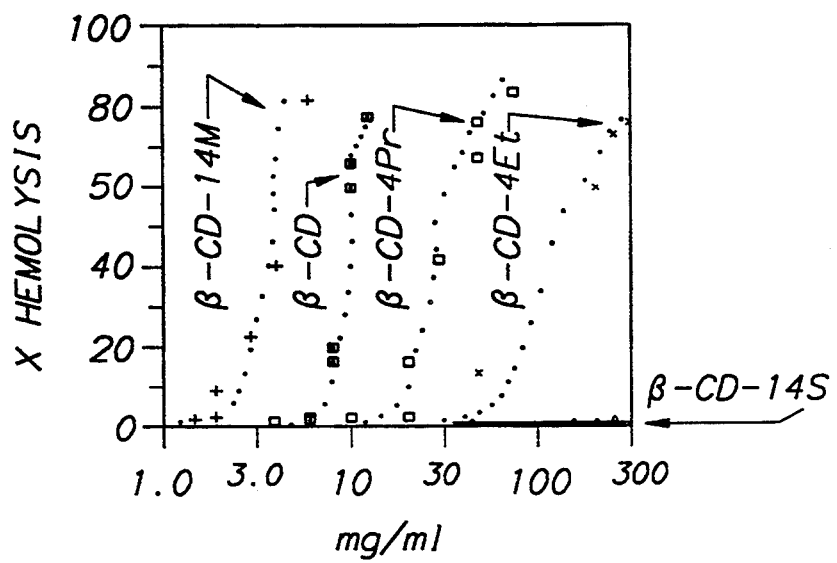

FIG. 2 graphically illustrates the hemolytic effects of two hydroxyalkyl substituted cyclodextrins, 2-hydroxyethyl-β-cyclodextrin (B-CD-4-Et) and 2-hydroxypropyl-β-cyclodextrin (B-CD-4Pr) in comparison to the polyanionically substituted cyclodextrin β-cyclodextrin-tetradecasulfate sodium (β-CD-14s) on fresh human blood to which about 0.47% sodium citrate was added. As shown in FIG. 2, β-CD-14s exhibits no undesirable hemolytic properties even at a concentration of hundreds of mg/ml. Note that the use of logarithmic scale to report data for β-CD-14s was necessary to accurately demonstrate the absence of hemolysis at the high concentrations tested.

The anionically substituted cyclodextrins are preferred, at least in part, because of the relative uniformity and ease of production of such compounds. Although Applicants do not intend to be bound by or limited to any particular theory of operation, the anionic oligosaccharides of this invention, and especially the simple and low molecular weight anionic oligosaccharides, are believed to be particularly effective because of the rigidity of their structure as compared to the flexibility of the chain-like dextrans, and especially because of the lack of end groups which increase their life-time in the biological environment, where sugar hydrolysis is fastest at end groups. Specifically preferred are the cyclodextrins designated by α-, β- and γ- prefixes, referring to the cyclodextrin having a ring of 6, 7, and 8 glucose sugar units, respectively, after addition of about 2 anionic groups, preferably sulfate groups, in place of hydroxyl groups. The resulting preferred, polyanionically substituted oligosaccharides have molecular weights of from about 1600 to about 4000.

Applicants have surprisingly and importantly found that the methods and compositions of the present invention prevent hemolytic action of hemolysis inducing cyclodextrin compositions compounds themselves, such as β-CD-14M, β-CD-4-Et and β-CD-4Pr, thus enabling such cyclodextrins to perform other useful functions at concentrations which would otherwise cause hemolytic action. More specifically, cyclodextrins (CDs) are being used for a growing number of pharmacological and therapeutic applications. CDs are cyclic doughnut shaped oligosaccharides of 6, 7 or 8 glucopyranose units (α-, β- and γ-cyclodextrins, respectively). The large number of hydroxyl groups (3 per glucose unit), located peripherally, provide water solubility. The central cavities are hydrophobic and can, by inclusion, complex hydrophobic molecular entities. This structure of cyclodextrins has been advantageously employed to form water soluble inclusion compounds, thereby providing a way to store, dissolve and deliver in an aqueous solution more of a pharmaceutical agent than could be otherwise accomplished by its limited solubility. The amount of agent that can thus be complexed and delivered, however, has heretofore been limited by the amount of the host cyclodextrin in the composition. That is, the heretofore used CDs have themselves possessed hemolytic activity which severely limited their usefulness as solubility enhancing agents.

It has been learned that the heretofore used CDs cause hemolysis at concentrations in excess of about 2–3 Mm. Thus, despite the growing interest in potential applications of CDs, the induction of hemolysis has heretofore been considered as limiting their utility for any purpose involving contact with erythrocytes. The hemolytic effects of non-anionic β-Cds are graphically depicted in FIGS. 1 and 2. As shown in FIG. 1, β-CD and a methyl substituted β-CD derivative thereof (β-CD-14M) both induce hemolysis of erythrocytes at relatively low concentration, that is, at about 6 mg/ml for β-CD and about 2 mg/ml for β-CD-14M. Hydroxyalkyl groups can lower but not eliminate hydrolyric hemolytic activity.

FIG. 2 graphically depicts the results of a study comparing the hemolytic effects of two other non-anionic Cds, β-CD-Et and β-CD-4Pr with those of the polysulfated CD, β-CD-14s. The ethyl and propyl substituted non-anionic CDs induced hemolysis at low concentrations. In comparison, substantially no hemolysis was observed with β-CD-14s even at concentrations as high as about 300 mg/ml.

Thus, Applicants have discovered that polyanionic oligosaccharides such as polyanionic cyclodextrin exhibit substantially no hemolytic activity, as shown in FIG. 2. Moreover, Applicants have discovered that anionically substituted oligosaccharides, and preferably polyanionically substituted cyclodextrin, can inhibit hemolysis caused by other agents. The compositions and methods of this invention thus allow the improvement or extension of the uses of non-anionically substituted cyclodextrins such as the aforementioned application of cyclodextrins for the delivery of sparsely soluble agents.

It will be apparent from this and the following description that anionic oligosaccharides, and especially the polyanionic oligosaccharides, such as polyanionic cyclodextrins, provide an effective means for protecting blood and blood products from undesired hemolysis.

I. THE METHODS

The methods of the present invention are based, at least in part, upon Applicants' discovery that anionic oligosaccharides, such as polyanionic β-cyclodextrins, are useful for protecting erythrocytes from the hemolytic effects of a wide array of otherwise hemolysis inducing agents. As the term is used herein, hemolysis inducing agent refers to any compound or composition tending to cause lysis of erythrocytes. As is known to those skilled in the art, certain therapeutic agents such as chlorpromazine, and other phenothiazines, perazines, tiamulin, flurbiprofen, and many others are hemolysis inducing agents. Blood and blood products also sometimes come into contact with other hemolysis inducing agents, such as incidental irritants present in the blood due to disease states or the intrusion of external irritants which may result, for example, from the normal storage of blood.

Thus, the present invention provides methods of using anionic oligosaccharides, and preferably polyanionic oligosaccharides, for protecting erythrocytes from hemolysis. According to one embodiment of the present methods, erythrocytes which are subject to hemolysis as the result of exposure to a hemolysis inducing agent are contacted by an anionic oligosaccharide, and preferably polyanionic oligosaccharides, in amounts effective to reduce the hemolytic effect of the hemolysis inducing agent. According to other embodiments, the present methods require contacting the hemolysis inducing agent with an anionic oligosaccharide, and preferably a polyanionic oligosaccharide, in an amount effective to reduce the hemolytic activity of the hemolysis inducing agent.

It is contemplated that the reduction in hemolysis attributable to the present methods may vary widely within the scope hereof, depending upon several factors, such as the particular type and amount of hemolysis inducing agent. It is generally preferred, however, that the anionic oligosaccharide be present in an amount effective to substantially reduce hemolysis caused by the hemolysis inducing agent. According to certain preferred embodiments, the anionic oligosaccharide is present in an amount effective to reduce the hemolysis caused by the hemolysis inducing agent by at least 30% relative the hemolysis caused by such agent in the absence of the oligosaccharide of the present invention.

According to certain preferred embodiments of the present invention, the contacting step of the present methods comprises contacting the erythrocytes with an isotonic solution containing anionic oligosaccharide, and preferably polyanionic oligosaccharide. It is contemplated that the concentration of anionic oligosaccharide in such solutions may vary widely within the scope of the present invention, depending upon factors such as the type and amount of hemolysis inducing agent being used. It is preferred, however, that the concentration of the anionic oligosaccharide in the isotonic solution be from about 5 mg/ml to above about 200 mg/ml, with concentrations of from about 20 mg/ml to about 100 mg/ml being even more preferred.

Suitable polyanionic oligosaccharides include those substituted with multiple anions per molecule, preferably about two or more substitutions per sugar unit. As indicated hereinbefore, substituent groups preferably include sulfate, phosphate, carboxylate or combinations thereof, with sulfate being preferred. $\beta$-cyclodextrins are presently preferred oligosaccharides for this purpose. Other substituents may also be present in addition to the preferred anions.

II. THE COMPOSITIONS

The present invention provides compositions useful for preventing the hemolytic effect of hemolysis inducing agents. Furthermore, the present compositions have no substantial hemolytic activity. Applicants have found that these desirable characteristics are imparted to the present compositions by the inclusion therein of a protective agent which is characterized by substantially no hemolytic activity, even when present in relatively high concentrations, and by the ability to prevent or substantially inhibit the hemolytic activity of hemolysis inducing agents. Applicants have found that preferred protective agents comprise anionic oligosaccharide.

In view of the disclosure contained herein, those skilled in the art will appreciate that the protective agent in general, and the anionic oligosaccharide in particular, will have beneficial effect in a wide variety of applications. It is therefore contemplated that the compositions of this invention may take numerous and varied forms, depending upon the particular circumstance of each application. The protective agent may be incorporated into a solid pill or a liquid solution. Furthermore, it will be appreciated that the protective agent may be utilized or administered in a variety of ways. For example, the protective agent may be included in the same composition which includes the hemolysis inducing agent or it may be incorporated in a separate composition and coadministered with the hemolysis inducing agent. In general, therefore, the compositions of the present invention preferably comprise a protective agent and a suitable, non-toxic, physiologically acceptable carrier for said protective agent. As the term is used herein, carrier refers broadly to materials which facilitate administration or use of the present compositions for the inhibition of hemolysis. In certain embodiments, the protective agent and the hemolysis inducing agent are incorporated in the same carrier. In other embodiments, the carrier component may comprise the blood which is to be protected. In such embodiments, the protective agent may be present to protect the blood from hemolytic agents which may later be introduced into the blood. Compositions comprising all such carriers are within the scope hereof.

A. Non-Hemolytic Compositions

The present invention provides non-hemolytic compositions suitable for administration to mammals, including humans, comprising at least one water soluble pharmaceutically active, hemolysis inducing agent and a polyanionic oligosaccharide, which is preferably a cyclodextrin. The oligosaccharide is preferably present in the composition in amounts effective to substantially reduce the hemolytic effect of such hemolysis inducing agent. In general, the compositions preferably comprise anionic oligosaccharide in an amount effective to reduce hemolysis by at least about 30% relative to the hemolytic activity of said agent in the absence the anionic oligosaccharide.

The present invention also provides compositions comprising a pharmaceutically active agent of sparse water solubility and an anionic oligosaccharide for improving the solubility of the agent without increasing the hemolytic activity of the composition. Such compositions may optionally include other solubility enhancers. For compositions containing solubility enhancers having hemolytic activity, such as non-anionic cyclodextrin, the anionic oligosaccharide are preferably present in amounts effective to substantially reduce the hemolytic activity of the composition, for example by at least about 30% relative to the hemolytic activity of said composition in the absence of the anionic oligosaccharide.

As mentioned hereinbefore, the effective compositions of this invention are best administered in a suitable carrier, which must be non-toxic and physiologically acceptable, such as water or normal saline solutions. Compositions containing mixtures of the active agents can be employed. The amount of polyanionic oligosaccharide to be used will depend on the hemolytic activity level to be reduced. For compositions in which the carrier comprises an aqueous solution, however, the amount will preferably be such as to create a solution concentration of between about 5 and about 200 mg/ml, and even more preferably between about 10 and about 100 mg/ml.

Cyclodextrins are the preferred oligosaccharides. In particular, the beta-cyclodextrins are preferred because of the effectiveness of the anionic products thereof, and because of the relative ease of availability of the cyclodextrin starting material.

The most effective and therefore most desirable anionic cyclodextrins are those with at least about ten sulfate groups per molecule, which corresponds to about 1.4 sulfate groups per sugar unit, or more.

Beta-cyclodextrin tetradecasulfate is a preferred and desirable material in and for purposes of the present invention. It represents a cyclic oligosaccharide having seven sugar units bearing in the average about two sulfate groups per unit.

B. Compositions Useful For Storage Of Blood And Blood Product Preparations

According to another embodiment of the present invention, the non-hemolytic properties of the present anionic oligosaccharides are employed to provide compositions useful to prevent or substantially inhibit hemolysis of materials containing erythrocytes. For example, the present compositions are useful in connection with the storage and handling of blood, blood-containing products, tissues or organs. A blood storage composition of the invention preferably comprises a polyanionic oligosaccharide and at least one blood storage additive. Such compositions preferably comprise anionic oligosaccharide in an amount effective to extend useful life of the blood storage composition by at least about 20% relative to the useful life of the composition in the absence of said anionic oligosaccharide. The polyanionic cyclodextrins are preferred oligosaccharides.

The blood product of the invention comprises erythrocytes and an anionic oligosaccharide. Such blood products may further comprise a blood storage additive. Such blood storage additives include generally, anti-coagulants and nutritive ingredients. Typical additives include sodium chloride, citric acid, sodium citrate, glucose, sodium dihydrogenphosphate, glycerin, folic acid emulsion, adenine and L-ascorbic acid phosphate, although any additive known to those skilled in the art is contemplated. The concentration of blood storage additive in the composition depends upon a combination of factors including the amount of blood product and the nature of the additive or combination thereof used. For example, for a volume of one pint of blood stored in a solution containing sodium citrate, a concentration of about 10 to about 100 mg/ml is suitable. Determining effective amounts of such additives is considered well within the purview of the skilled artisan. Suitable and preferred polyanionic cyclodextrins are the same as those previously mentioned.

III. EXAMPLES

The following examples are provided to illustrate but not limit this invention. Unless explicitly stated otherwise, hemolytic activity was measured by the procedure described by I. Jodal et al., Proceedings of the Fourth International Symposium on Cyclodextrins, O. Huber and J. Szejtli, Eds., 421–425, Kluwer Academic Publishers, Boston (1988), which is incorporated herein by reference.

For each of the examples which follow, sodium citrate was added about (0.47%) to fresh human blood collected from healthy laboratory personnel. After centrifugation (10 min., 400×G) to separate the erythrocytes from other blood components, the supernatant erythrocyte fraction was then recentrifuged and washed twice with isotonic phosphate buffer. The erythrocytes were diluted with that buffer to a 10% hematocrit value to obtain an erythrocyte suspension. Test material and erythrocytes were mixed as follows: about 3.6, 1.8, and 0.9 ml of a test material solution was mixed with about 0.4, 0.2 and 0.1 ml, respectively, of erythrocyte suspension and then incubated for about 15 minutes each at about 37° C., followed by two centrifugations for two minutes each at about 4000 G The resulting supernatants were measured for absorbance at 543 nm using a Gilford spectrophotometer. The percent of hemolysis was determined by reference to two control samples. The first sample contained erythrocytes and isotonic saline. This first sample served as a zero blank. The second sample was identical to the first but had been sonicated to provide a value for 100% hemolysis.

A. Examples 1 to 9

The following examples will illustrate the strong hemolytic effect of a phenothiazine derivative and neuroleptic drug: chloropromazine (CPZ).

TABLE I

| Example # | CPZ Concentration mg/ml | % Hemolysis |
|---|---|---|
| 1 | 0.15 | 4.9 |
| 2 | 0.25 | 7.0 |
| 3 | 0.30 | 88 |
| 4 | 0.40 | 96 |

Examples 1 to 4 illustrate the strong hemolytic activity of CPZ which leads to complete hemolysis at concentrations approaching 0.5 mg/ml of CPZ.

Examples 5 to 9 show how, in contrast to the findings in Example 1 to 4, much higher concentrations of CPZ can be tolerated if $\beta$-cyclodextrin polysulfate (CD having 14 sulfate groups per molecule) is added.

TABLE II

| Example # | CPZ Concentration mg/ml | CDS Concentration mg/ml | Hemolysis % |
|---|---|---|---|
| 5 | 1.0 | 50 | 5.9 |
| 6 | 2.0 | 50 | 90 |
| 7 | 2.0 | 60 | 73 |
| 8 | 2.0 | 70 | 2.3 |
| 9 | 2.0 | 80 | 3.1 |

It is seen that the use of about 70 mg/ml of CDS is sufficient to allow the use of about 2.0 mg/ml concentration of CPZ with negligible hemolytic effect, while without CDS addition, about one-fifth of this CPZ concentration would already result in the substantially complete hemoglobin (Example 4.

B. Examples 10 to 13

These examples illustrate the hemolysis inhibiting effect of increasing amounts of $\beta$-CD-14s on a solution of about 15 mg/ml of an unsubstituted $\beta$-cyclodextrin itself (CD). As shown in Table III, at a concentration of 50 mg/ml, $\beta$-CD-14s reduced the level of hemolysis by about 41%, and 150 mg/ml reduced hemolysis from nearly about 90% to about 3%, or about 30 fold.

TABLE III

| Example # | Concentration in mg/ml | | % Hemolysis |
|---|---|---|---|
| | CD | $\beta$-CD-14s | |
| 10 | 15 | 0 | 90 |
| 11 | 15 | 50 | 49 |
| 12 | 15 | 100 | 19 |
| 13 | 15 | 150 | 3 |

C. Examples 14 to 16

These examples illustrate the hemolysis inhibiting effect of increasing amounts of $\beta$-CD-14s on a solution of 75 mg/ml hydroxypropyl cyclodextrin (Pr OH—CD). As shown in Table I, at a concentration of 100 mg/ml $\beta$-CD-14s, only 3% hemolysis was observed as compared with 64% hemolysis in the absence of $\beta$-CD-14s, representing an at least 20 fold improvement, that is, reduction in hemolysis.

TABLE IV

| Example # | Concentration in mg/ml | | % Hemolysis |
|---|---|---|---|
| | Pr-OH-CD | $\beta$-CD-14s | |
| 14 | 75 | 0 | 64 |

TABLE IV-continued

| Example # | Concentration in mg/ml | | % Hemolysis |
| | Pr-OH-CD | β-CD-14s | |
| --- | --- | --- | --- |
| 15 | 75 | 50 | 20 |
| 16 | 75 | 100 | 3 |

Examples 1 to 9 have illustrated the capability of a sulfated oligosaccharide, beta-cyclodextrin poly sulfate (CDS), to inhibit the hemolysis caused by a pharmaceutical agent in solution. Examples 10 to 13 have illustrated the analogous capability of the polyanionic oligosaccharide to inhibit hemolysis induced by the unsubstituted cyclodextrin, and examples 14 to 16 have illustrated the same inhibition when hemolysis is caused by a nonanionic substituted cyclodextrin.

The following examples will illustrate the analogous capability of protection by the anionic saccharide of this invention to hemolysis induced by an entirely different family of hemolytic irritants, namely by solid, non-soluble particulates present as a dispersion. Best known are silica, silicates, clays, asbestos, etc.

Examples 17 to 19 illustrate this for particles of clay. The clay used in these examples is montmorillonite (Mineral Colloid BP, from Southern Clay Products, Gonzales, Texas). Montmorillonite was chosen because it is known to have typically high hemolytic activity, as exemplified by D. W. Oscarson et al., in "Lysis of Erithrocytes by Silicate Minerals," Clay and Clay Minerals, Vol. 34, pages 74–80 (1986)

TABLE V

| Example # | | Clay mg/ml | CDS mg/ml | Hemolysis % (*) |
| --- | --- | --- | --- | --- |
| 14 | 17 | 1.5 | 0 | 64, 66, 76 |
| 15 | 18 | 1.5 | 25 | 44, 54, 53 |
| 16 | 19 | 1.5 | 50 | 22, 20, 20 |

(*) data from three sets of runs

The findings illustrated by examples 1 to 19, taken together, demonstrate the effectiveness of the protective effect afforded in the present invention against a variety of compositionally entirely different hemolytic irritants. In fact inspection of the data indicates that the quantitative magnitude of effective concentration of the protective agent of this invention which will provide substantial hemolysis reduction is very much the same for all the vast variety of irritants. This demonstrates that the action of the materials of this invention is upon the erythrocytes, and is not seen to be a specific action on specific compound structures of the irritant.

While we do not wish to be limited by theory, or dismiss the possibility of exceptions for some irritants, the most effective concentrations seen for the use of oligosaccharides of this invention are for the use of concentrations between about 5 and about 200 mg/ml, and preferably between about 20 and about 100 mg/ml.

As pointed out further above, cyclodextrins and some of its derivatives have been used, by virtue of their molecular complexing or inclusion capabilities, to carry pharmaceuticals of low solubility into aqueous solution, as well as to provide limited protection against their hemolytic action, if they have any. The applications of that principle is limited in concentration by the known hemolytic effects of the very cyclodextrins employed as carriers or protectors. This will be illustrated specifically by the following examples 20 to 23.

TABLE VI

| Example # | Concentrations | | | | molar ratio CD/CPZ | Hemolysis # |
| | CPZ | | CD | | | |
| | mg/ml | mM | mg/ml | mM | | |
| --- | --- | --- | --- | --- | --- | --- |
| 20 | 0.5 | 1.5 | 5.0 | 4.0 | 2.7 | 6.5 |
| 21 | 0.75 | 2.25 | 7.5 | 6.0 | 2.7 | 21 |
| 22 | 1.0 | 3.0 | 10 | 8.0 | 2.7 | 80 |
| 23 | 1.0 | 3.0 | +50 mg/ml CDS- | | | 8.5 |

It is seen from example 20 that beta-cyclodextrin (CD) provides considerable protection from hydrolysis by CPZ, as 0.5 mg/ml of CPZ would cause near 100% hemolysis. According to the prior art this protection is afforded by the complexation by and inclusion in the excess molar quantity of beta-cyclodextrin. Examples 21 and 22 show that this same protection is lost as higher concentrations are attempted inasmuch as the protector itself, as shown before becomes hemolytically active. Yet, example 23 shows how even at the highest concentration of both the agent (CPZ) and the anionic protector of the present invention (CDS), the composition exhibited substantially reduced hemolytic activity.

From these results and illustrations it is clear that the addition of polyanionic oligosaccharides to a composition contacted with blood is effective in protecting erythrocytes against hemolytic action due to a variety of causes. It is contemplated therefore to use this invention for protection against hemolysis in a variety of applications in which hemolysis can otherwise occur, such as in the ministration of compositions for pharmaceutical purposes, for delivery of soluble or sparsely soluble pharmaceutical agents with or without additives to aid the solubility or other properties of such agents, or for the storage and preservation of erythrocytes, and other applications in which inhibition of hemolysis is to be effected.

The preferred materials in this invention are oligosaccharides of between about 5 and about 10 sugar units. The preferred degree of anionic substitution is at least about 1.5 anionic substitutions per sugar unit. The preferred saccharide for this purpose is a cyclic oligosaccharide. The preferred type of ionic substitutions are sulfates and phosphates. The concentrations of use will generally be between about 5 and about 200 mg/ml, but preferably between about 20 and about 100 mg/ml. A preferred specific material is beta-cyclodextrin bearing at least about 10 anionic substitutions, preferably sulfate per molecule of cyclodextrin.

What is claimed is:

1. A method of preventing hemolysis of erythrocytes comprising contacting the erythrocytes with an anionic oligosaccharide.

2. The method of claim 1 wherein the anionic oligosaccharide comprises polyanionic oligosaccharide.

3. The method of claim 2 wherein the polyanionic oligosaccharide has from about 5 to about 10 sugar units.

4. The method of claim 2 wherein the polyanionic oligosaccharide is an α-, β- or γ-cyclodextrin.

5. The method of claim 1 wherein the oligosaccharide has from about 1.5 to about 3.0 anionic groups per sugar unit.

6. The method of claim 1 wherein the anionic constituents are selected from the group consisting of sulfate, carboxylate, phosphate, and combinations of two or more of these.

7. The method of claim 2 wherein the polyanionic oligosaccharide is beta-cyclodextrin polysulfate having at least about 10 sulfate group substituents per molecule.

8. The method of claim 7 wherein the beta-cyclodextrin polysulfate is tetradecasulfate.

9. The method of claim 2 wherein the contacting step comprises contacting the erythrocytes with an isotonic solution containing a polyanionic oligosaccharide present at a concentration of from about 5 to about 300 mg/ml.

10. The method of claim 9 wherein the polyanionic oligosaccharide is present at a concentration of from about 20 to about 150 mg/ml.

* * * * *